United States Patent
Cook

(10) Patent No.: US 12,226,143 B2
(45) Date of Patent: Feb. 18, 2025

(54) UNIVERSAL SURGICAL FOOTSWITCH TOGGLING

(71) Applicant: Covidien LP, Mansfield, MA (US)

(72) Inventor: Henry D. Cook, Lyons, CO (US)

(73) Assignee: Covidien LP, Mansfield, MA (US)

( * ) Notice: Subject to any disclaimer, the term of this patent is extended or adjusted under 35 U.S.C. 154(b) by 867 days.

(21) Appl. No.: 17/354,036

(22) Filed: Jun. 22, 2021

(65) Prior Publication Data

US 2021/0393313 A1    Dec. 23, 2021

Related U.S. Application Data

(60) Provisional application No. 63/042,163, filed on Jun. 22, 2020.

(51) Int. Cl.
    *A61B 18/12*    (2006.01)
    *A61B 17/00*    (2006.01)
    *A61B 18/00*    (2006.01)

(52) U.S. Cl.
    CPC .  *A61B 18/1206* (2013.01); *A61B 2017/00115* (2013.01); *A61B 2017/00973* (2013.01); *A61B 2018/00607* (2013.01); *A61B 2018/00839* (2013.01); *A61B 2018/00928* (2013.01); *A61B 2018/00994* (2013.01); *A61B 2018/1253* (2013.01); *A61B 2018/126* (2013.01)

(58) Field of Classification Search
    CPC .......... A61B 2018/00994; A61B 34/74; A61B 90/37; A61B 2017/00973
    See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |

(Continued)

FOREIGN PATENT DOCUMENTS

| | | |
|---|---|---|
| DE | 179607 C | 11/1906 |
| DE | 390937 C | 3/1924 |

(Continued)

OTHER PUBLICATIONS

US 6,878,148 B2, 04/2005, Goble et al. (withdrawn)

(Continued)

*Primary Examiner* — Sean W Collins

(57) ABSTRACT

An electrosurgical system includes an electrosurgical generator having a radio frequency source configured to operate in a plurality of modes and a controller configured to control the radio frequency source to output a radio frequency waveform corresponding to a mode from the plurality of modes. The system also includes a footswitch assembly coupled to the electrosurgical generator. The footswitch assembly includes a footswitch in communication with the controller. The footswitch is configured to output a footswitch activation signal to activate the radio frequency source. The footswitch assembly also includes a mode select button, which upon activation, is configured to instruct the controller to enter a mapping state during which the controller assigns an activation command for one mode from the plurality of modes to the footswitch.

20 Claims, 5 Drawing Sheets

(56) References Cited

U.S. PATENT DOCUMENTS

| | | |
|---|---|---|
| 1,945,867 A | 2/1934 | Rawls |
| 2,693,106 A | 6/1951 | Henry |
| 2,827,056 A | 3/1958 | Degelman |
| 2,849,611 A | 8/1958 | Adams |
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |

(56) References Cited

U.S. PATENT DOCUMENTS

| | | |
|---|---|---|
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,057,105 A | 10/1991 | Malone et al. |
| 5,067,953 A | 11/1991 | Feucht |
| 5,075,839 A | 12/1991 | Fisher et al. |
| 5,078,153 A | 1/1992 | Nordlander et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,113,116 A | 5/1992 | Wilson |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,216,338 A | 6/1993 | Wilson |
| 5,230,623 A | 7/1993 | Guthrie et al. |
| 5,233,515 A | 8/1993 | Cosman |
| 5,234,427 A | 8/1993 | Ohtomo et al. |
| 5,244,462 A | 9/1993 | Delahuerga et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,269,780 A | 12/1993 | Roos |
| 5,271,413 A | 12/1993 | Dalamagas et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,396,194 A | 3/1995 | Williamson et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen et al. |
| 5,445,638 A | 8/1995 | Rydell et al. |
| 5,448,466 A | 9/1995 | Erckert |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,498,261 A | 3/1996 | Strul |
| 5,500,012 A | 3/1996 | Brucker et al. |
| 5,500,616 A | 3/1996 | Ochi |

(56) References Cited

U.S. PATENT DOCUMENTS

| | | |
|---|---|---|
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |
| 5,542,916 A | 8/1996 | Hirsch et al. |
| 5,545,161 A | 8/1996 | Imran |
| 5,554,172 A | 9/1996 | Horner et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,693,082 A | 12/1997 | Warner et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,835 A | 8/1999 | Mackey |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,002,968 A | 12/1999 | Edwards |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |

(56) References Cited

U.S. PATENT DOCUMENTS

| | | |
|---|---|---|
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,780 A | 5/2000 | Gough et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,089,864 A | 7/2000 | Buckner et al. |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,104,248 A | 8/2000 | Carver |
| 6,106,524 A | 8/2000 | Eggers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven et al. |
| 6,123,701 A | 9/2000 | Nezhat |
| 6,123,702 A | 9/2000 | Swanson et al. |
| 6,132,429 A | 10/2000 | Baker |
| 6,139,349 A | 10/2000 | Wright |
| 6,142,992 A | 11/2000 | Cheng et al. |
| 6,144,937 A | 11/2000 | Ali |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,165,173 A | 12/2000 | Kamdar et al. |
| 6,171,304 B1 | 1/2001 | Netherly |
| 6,173,713 B1 | 1/2001 | Dawson |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,200,314 B1 | 3/2001 | Sherman |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman et al. |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu et al. |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,259,937 B1 | 7/2001 | Schulman et al. |
| 6,261,285 B1 | 7/2001 | Novak et al. |
| 6,261,286 B1 | 7/2001 | Goble et al. |
| 6,267,760 B1 | 7/2001 | Swanson |
| 6,270,497 B1 | 8/2001 | Sekino et al. |
| 6,273,886 B1 | 8/2001 | Edwards et al. |
| 6,275,786 B1 | 8/2001 | Daners |
| 6,287,304 B1 | 9/2001 | Eggers et al. |
| 6,293,941 B1 | 9/2001 | Strul et al. |
| 6,293,942 B1 | 9/2001 | Goble et al. |
| 6,293,943 B1 | 9/2001 | Panescu et al. |
| 6,296,636 B1 | 10/2001 | Cheng et al. |
| 6,304,138 B1 | 10/2001 | Johnson |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |
| 6,341,981 B1 | 1/2002 | Gorman |
| 6,350,262 B1 | 2/2002 | Ashley |
| 6,350,263 B1 | 2/2002 | Wetzig et al. |
| 6,358,245 B1 | 3/2002 | Edwards et al. |
| 6,364,877 B1 | 4/2002 | Goble et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,387,092 B1 | 5/2002 | Burnside et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,424,186 B1 | 7/2002 | Quimby et al. |
| 6,426,886 B1 | 7/2002 | Goder |
| 6,427,089 B1 | 7/2002 | Knowlton |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock et al. |
| 6,458,122 B1 | 10/2002 | Pozzato |
| 6,464,689 B1 | 10/2002 | Qin et al. |
| 6,464,696 B1 | 10/2002 | Oyama et al. |
| 6,468,270 B1 | 10/2002 | Hovda et al. |
| 6,468,273 B1 | 10/2002 | Leveen et al. |
| 6,469,481 B1 | 10/2002 | Tateishi |
| 6,482,201 B1 | 11/2002 | Olsen et al. |
| 6,485,487 B1 | 11/2002 | Sherman |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul et al. |
| 6,511,476 B2 | 1/2003 | Hareyama |
| 6,511,478 B1 | 1/2003 | Burnside et al. |
| 6,514,251 B1 | 2/2003 | Ni et al. |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton et al. |
| 6,565,559 B2 | 5/2003 | Eggleston |

(56) References Cited

U.S. PATENT DOCUMENTS

| | | |
|---|---|---|
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wardell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano et al. |
| 6,645,198 B1 | 11/2003 | Bommannan et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,514 B2 | 11/2003 | Ellman et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim et al. |
| 6,693,782 B1 | 2/2004 | Lash |
| 6,695,837 B2 | 2/2004 | Howell |
| 6,696,844 B2 | 2/2004 | Wong et al. |
| 6,700,076 B2 | 3/2004 | Sun et al. |
| 6,712,813 B2 | 3/2004 | Ellman et al. |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano et al. |
| 6,733,495 B1 | 5/2004 | Bek et al. |
| 6,733,498 B2 | 5/2004 | Paton et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano et al. |
| 6,860,881 B2 | 3/2005 | Sturm et al. |
| 6,864,686 B2 | 3/2005 | Novak et al. |
| 6,875,210 B2 | 4/2005 | Refior et al. |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 6,997,935 B2 | 2/2006 | Anderson et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | De Ruijter et al. |
| 7,192,427 B2 | 3/2007 | Chapelon et al. |
| 7,195,627 B2 | 3/2007 | Amoah et al. |

(56) References Cited

U.S. PATENT DOCUMENTS

| | | |
|---|---|---|
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,468,499 B2 | 12/2008 | Canini et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,573,693 B2 | 8/2009 | Hornung |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,736,359 B2 | 6/2010 | McPherson |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,863,984 B1 | 1/2011 | Behnke |
| 7,864,129 B2 | 1/2011 | Konishi |
| 7,879,029 B2 | 2/2011 | Jimenez |
| 7,879,033 B2 | 2/2011 | Sartor et al. |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 8,038,676 B2 | 10/2011 | Fischer |
| 8,070,746 B2 | 12/2011 | Orton et al. |
| 8,080,008 B2 | 12/2011 | Wham et al. |
| 8,083,735 B2 | 12/2011 | Morris |
| 8,096,961 B2 | 1/2012 | Orszulak et al. |
| 8,104,596 B2 | 1/2012 | Kim et al. |
| 8,105,323 B2 | 1/2012 | Buysse et al. |
| 8,113,057 B2 | 2/2012 | Orszulak et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,187,262 B2 | 5/2012 | Orszulak |
| 8,200,317 B2 | 6/2012 | Baxi et al. |
| 8,202,271 B2 | 6/2012 | Orszulak |
| 8,211,100 B2 | 7/2012 | Podhajsky et al. |
| 8,216,219 B2 | 7/2012 | Desinger et al. |
| 8,216,220 B2 | 7/2012 | Jensen et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,231,614 B2 | 7/2012 | Dunning et al. |
| 8,231,616 B2 | 7/2012 | McPherson et al. |
| 8,235,917 B2 | 8/2012 | Joseph et al. |
| 8,241,278 B2 | 8/2012 | Sartor |
| 8,242,782 B2 | 8/2012 | Brannan et al. |
| 8,248,075 B2 | 8/2012 | Brannan et al. |
| 8,257,349 B2 | 9/2012 | Orszulak |
| 8,257,350 B2 | 9/2012 | Marion |
| 8,262,652 B2 | 9/2012 | Podhajsky |
| 8,267,928 B2 | 9/2012 | Orszulak et al. |
| 8,267,929 B2 | 9/2012 | Wham et al. |
| 8,287,528 B2 | 10/2012 | Wham et al. |
| 8,287,529 B2 | 10/2012 | Orszulak |
| 8,292,883 B2 | 10/2012 | Kabaya et al. |
| 8,298,223 B2 | 10/2012 | Wham et al. |
| 8,303,337 B2 | 11/2012 | Ballard et al. |

(56) References Cited

U.S. PATENT DOCUMENTS

| | | |
|---|---|---|
| 8,303,580 B2 | 11/2012 | Wham et al. |
| 8,333,759 B2 | 12/2012 | Podhajsky |
| 8,346,370 B2 | 1/2013 | Haley et al. |
| 8,353,903 B2 | 1/2013 | Podhajsky |
| 8,353,905 B2 | 1/2013 | Jensen et al. |
| 8,377,053 B2 | 2/2013 | Orszulak |
| 8,377,054 B2 | 2/2013 | Gilbert |
| 8,382,751 B2 | 2/2013 | Gilbert et al. |
| 8,398,627 B2 | 3/2013 | Hosier |
| 8,403,924 B2 | 3/2013 | Behnke et al. |
| 8,409,186 B2 | 4/2013 | Behnke et al. |
| 8,454,590 B2 | 6/2013 | Smith |
| 8,460,284 B2 | 6/2013 | Aronow et al. |
| 8,469,956 B2 | 6/2013 | McKenna et al. |
| 8,475,447 B2 | 7/2013 | Orszulak et al. |
| 8,485,993 B2 | 7/2013 | Orszulak et al. |
| 8,486,061 B2 | 7/2013 | Podhajsky |
| 8,512,232 B2 | 8/2013 | Rothberg et al. |
| 8,523,855 B2 | 9/2013 | Keppel |
| 8,540,709 B2 | 9/2013 | Allen |
| 8,542,019 B2 | 9/2013 | Brannan et al. |
| 10,406,690 B1 | 9/2019 | Blankespoor |
| 10,573,713 B2 | 2/2020 | Wen et al. |
| 10,761,524 B2 | 9/2020 | Wallace |
| 11,242,458 B2 | 2/2022 | Takada et al. |
| 2002/0022836 A1 | 2/2002 | Goble et al. |
| 2002/0029036 A1 | 3/2002 | Goble et al. |
| 2003/0153908 A1 | 8/2003 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton et al. |
| 2004/0097912 A1 | 5/2004 | Gonnering |
| 2004/0133189 A1 | 7/2004 | Sakurai |
| 2004/0172016 A1 | 9/2004 | Bek et al. |
| 2004/0193021 A1 | 9/2004 | Zdeblick et al. |
| 2005/0004634 A1 | 1/2005 | Ricart et al. |
| 2005/0021020 A1 | 1/2005 | Blaha |
| 2005/0043828 A1* | 2/2005 | Tanaka .................. A61B 18/20 700/83 |
| 2005/0109111 A1 | 5/2005 | Manlove et al. |
| 2005/0109935 A1 | 5/2005 | Manlove et al. |
| 2005/0131390 A1 | 6/2005 | Heinrich et al. |
| 2006/0079774 A1 | 4/2006 | Anderson |
| 2006/0111711 A1 | 5/2006 | Goble |
| 2006/0155270 A1 | 7/2006 | Hancock |
| 2006/0161148 A1 | 7/2006 | Behnke |
| 2006/0191926 A1 | 8/2006 | Ray et al. |
| 2006/0224053 A1 | 10/2006 | Black et al. |
| 2006/0224152 A1 | 10/2006 | Behnke et al. |
| 2006/0291178 A1 | 12/2006 | Shih |
| 2007/0088413 A1 | 4/2007 | Weber et al. |
| 2007/0093801 A1 | 4/2007 | Behnke |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2008/0004619 A1 | 1/2008 | Malis et al. |
| 2008/0015563 A1 | 1/2008 | Hoey et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0132893 A1 | 6/2008 | D'Amelio et al. |
| 2008/0147056 A1 | 6/2008 | van der Weide et al. |
| 2008/0177199 A1 | 7/2008 | Podhajsky |
| 2008/0203997 A1 | 8/2008 | Foran et al. |
| 2008/0234574 A1 | 9/2008 | Hancock et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287943 A1 | 11/2008 | Weber et al. |
| 2008/0319350 A1 | 12/2008 | Wallace et al. |
| 2009/0018536 A1 | 1/2009 | Behnke |
| 2009/0030477 A1 | 1/2009 | Jarrard |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0234350 A1 | 9/2009 | Behnke et al. |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0248007 A1 | 10/2009 | Falkenstein et al. |
| 2009/0254077 A1 | 10/2009 | Craig |
| 2009/0259224 A1 | 10/2009 | Wham et al. |
| 2009/0292283 A1 | 11/2009 | Odom |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0082022 A1 | 4/2010 | Haley et al. |
| 2010/0082023 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0114090 A1 | 5/2010 | Hosier |
| 2010/0168572 A1 | 7/2010 | Sliwa et al. |
| 2010/0168730 A1 | 7/2010 | Hancock et al. |
| 2010/0168741 A1 | 7/2010 | Sanai et al. |
| 2010/0179533 A1 | 7/2010 | Podhajsky |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0228264 A1* | 9/2010 | Robinson ............ A61B 18/1206 606/130 |
| 2010/0268220 A1 | 10/2010 | Johnson et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert et al. |
| 2011/0071516 A1 | 3/2011 | Gregg |
| 2011/0071521 A1 | 3/2011 | Gilbert |
| 2011/0077631 A1 | 3/2011 | Keller |
| 2011/0077639 A1 | 3/2011 | Brannan et al. |
| 2011/0087213 A1 | 4/2011 | Messerly et al. |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0204903 A1 | 8/2011 | Gilbert |
| 2011/0208179 A1 | 8/2011 | Prakash et al. |
| 2011/0213354 A1 | 9/2011 | Smith |
| 2011/0213355 A1 | 9/2011 | Behnke, II |
| 2011/0230753 A1* | 9/2011 | Mahon .................. A61N 7/022 607/104 |
| 2011/0301607 A1 | 12/2011 | Couture |
| 2011/0318948 A1 | 12/2011 | Plaven et al. |
| 2011/0319881 A1 | 12/2011 | Johnston |
| 2012/0004703 A1 | 1/2012 | Deborski et al. |
| 2012/0010610 A1 | 1/2012 | Keppel |
| 2012/0022521 A1 | 1/2012 | Odom et al. |
| 2012/0028373 A1 | 2/2012 | Belen et al. |
| 2012/0029515 A1 | 2/2012 | Couture |
| 2012/0089139 A1 | 4/2012 | Wham et al. |
| 2012/0101491 A1 | 4/2012 | Blaha |
| 2012/0116268 A1 | 5/2012 | Orszulak et al. |
| 2012/0130256 A1 | 5/2012 | Buysse et al. |
| 2012/0150170 A1 | 6/2012 | Buysse et al. |
| 2012/0172866 A1 | 7/2012 | Behnke, II |
| 2012/0179156 A1 | 7/2012 | Behnke, II |
| 2012/0220997 A1 | 8/2012 | Johnston |
| 2012/0239020 A1 | 9/2012 | Cunningham |
| 2012/0239025 A1 | 9/2012 | Smith |
| 2012/0239026 A1 | 9/2012 | Orszulak et al. |

(56) References Cited

U.S. PATENT DOCUMENTS

| | | |
|---|---|---|
| 2012/0265194 A1 | 10/2012 | Podhajsky |
| 2012/0265195 A1 | 10/2012 | Gilbert |
| 2012/0303017 A1 | 11/2012 | Brannan et al. |
| 2012/0310241 A1 | 12/2012 | Orszulak |
| 2012/0316555 A1 | 12/2012 | Orszulak et al. |
| 2012/0316556 A1 | 12/2012 | Podhajsky |
| 2013/0006235 A1 | 1/2013 | Podhajsky et al. |
| 2013/0023867 A1 | 1/2013 | Collins |
| 2013/0023869 A1 | 1/2013 | Orszulak |
| 2013/0023870 A1 | 1/2013 | Collins |
| 2013/0023871 A1 | 1/2013 | Collins |
| 2013/0035679 A1 | 2/2013 | Orszulak |
| 2013/0041364 A1 | 2/2013 | Orszulak |
| 2013/0041367 A1 | 2/2013 | Wham et al. |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079763 A1 | 3/2013 | Heckel et al. |
| 2013/0158541 A1 | 6/2013 | Orszulak |
| 2013/0178848 A1 | 7/2013 | Gilbert et al. |
| 2013/0184698 A1 | 7/2013 | Behnke, II et al. |
| 2013/0184699 A1 | 7/2013 | Behnke, II et al. |
| 2013/0190750 A1 | 7/2013 | Behnke, II et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |
| 2014/0025064 A1 | 1/2014 | Collins et al. |
| 2014/0163431 A1 | 6/2014 | Orszulak et al. |
| 2017/0049501 A1* | 2/2017 | Guirguis ............ A61B 18/1402 |
| 2019/0117322 A1* | 4/2019 | Laubenthal ............ A61B 90/92 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0309942 A2 | 4/1989 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0503200 A2 | 9/1992 |
| EP | 0556705 A1 | 8/1993 |
| EP | 0569130 A1 | 11/1993 |
| EP | 0608609 A2 | 8/1994 |
| EP | 0617925 A1 | 10/1994 |
| EP | 0694291 A1 | 1/1996 |
| EP | 0836868 A2 | 4/1998 |
| EP | 0870473 A2 | 10/1998 |
| EP | 0878169 A1 | 11/1998 |
| EP | 0880220 A2 | 11/1998 |
| EP | 0882955 A1 | 12/1998 |
| EP | 0640317 B1 | 9/1999 |
| EP | 1051948 A2 | 11/2000 |
| EP | 1053720 A1 | 11/2000 |
| EP | 1146827 A1 | 10/2001 |
| EP | 1151725 A1 | 11/2001 |
| EP | 1157667 A2 | 11/2001 |
| EP | 1263181 A1 | 12/2002 |
| EP | 1278007 | 1/2003 |
| EP | 1293171 A2 | 3/2003 |
| EP | 1366724 A1 | 12/2003 |
| EP | 1472984 A1 | 11/2004 |
| EP | 1495712 A1 | 1/2005 |
| EP | 1500378 A1 | 1/2005 |
| EP | 1535581 A2 | 6/2005 |
| EP | 1594392 A2 | 11/2005 |
| EP | 1609430 A1 | 12/2005 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 A1 | 4/2007 |
| EP | 1810628 A1 | 7/2007 |
| EP | 1810630 A1 | 7/2007 |
| EP | 1810631 A2 | 7/2007 |
| EP | 1810632 A1 | 7/2007 |
| EP | 1810633 A2 | 7/2007 |
| EP | 1810634 A1 | 7/2007 |
| EP | 1849425 A1 | 10/2007 |
| EP | 1854423 A2 | 11/2007 |
| EP | 1862137 A1 | 12/2007 |
| EP | 1902681 A1 | 3/2008 |
| EP | 1994904 | 11/2008 |
| EP | 2025297 A2 | 2/2009 |
| EP | 2042116 A1 | 4/2009 |
| EP | 2100566 A1 | 9/2009 |
| EP | 2111812 A2 | 10/2009 |
| EP | 2156800 A1 | 2/2010 |
| EP | 2253286 A1 | 11/2010 |
| EP | 2301463 A1 | 3/2011 |
| EP | 2345454 A1 | 7/2011 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| GB | 607850 A | 9/1948 |
| GB | 702510 A | 1/1954 |
| GB | 855459 A | 11/1960 |
| GB | 902775 A | 8/1962 |
| GB | 1290304 A | 9/1972 |
| GB | 2154881 A | 9/1985 |
| GB | 2164473 A | 3/1986 |
| GB | 2214430 A | 9/1989 |
| GB | 2331247 A | 5/1999 |
| GB | 2358934 A | 8/2001 |
| GB | 2434872 A | 8/2007 |
| JP | 63005876 | 1/1988 |
| JP | 2002065690 A | 3/2002 |

(56) References Cited

FOREIGN PATENT DOCUMENTS

| | | |
|---|---|---|
| JP | 2005185657 A | 7/2005 |
| SU | 166452 | 11/1964 |
| SU | 727201 A2 | 4/1980 |
| WO | 9206642 | 4/1992 |
| WO | 9207622 A1 | 5/1992 |
| WO | 9320747 A1 | 10/1993 |
| WO | 9324066 A1 | 12/1993 |
| WO | 9410922 A1 | 5/1994 |
| WO | 9424949 A1 | 11/1994 |
| WO | 9428809 A1 | 12/1994 |
| WO | 9509577 A1 | 4/1995 |
| WO | 9518575 A1 | 7/1995 |
| WO | 9519148 A1 | 7/1995 |
| WO | 95/25472 A1 | 9/1995 |
| WO | 9525471 A2 | 9/1995 |
| WO | 9602180 A2 | 2/1996 |
| WO | 9604860 A1 | 2/1996 |
| WO | 9608794 A1 | 3/1996 |
| WO | 9618349 A2 | 6/1996 |
| WO | 9629946 A1 | 10/1996 |
| WO | 96/39088 A1 | 12/1996 |
| WO | 9639085 A1 | 12/1996 |
| WO | 9639086 A1 | 12/1996 |
| WO | 9639914 A1 | 12/1996 |
| WO | 9706739 A2 | 2/1997 |
| WO | 9706740 A2 | 2/1997 |
| WO | 9706855 A2 | 2/1997 |
| WO | 9710763 A1 | 3/1997 |
| WO | 9711648 A2 | 4/1997 |
| WO | 9717029 A1 | 5/1997 |
| WO | 97/43971 A2 | 11/1997 |
| WO | 98/07378 A1 | 2/1998 |
| WO | 9818395 A1 | 5/1998 |
| WO | 9827880 | 7/1998 |
| WO | 9912607 A1 | 3/1999 |
| WO | 9956647 A1 | 11/1999 |
| WO | 00/48672 A1 | 8/2000 |
| WO | 0054683 A1 | 9/2000 |
| WO | 0101847 | 1/2001 |
| WO | 02/00129 | 1/2002 |
| WO | 0211634 | 2/2002 |
| WO | 0232333 | 4/2002 |
| WO | 0232335 | 4/2002 |
| WO | 0245589 A2 | 6/2002 |
| WO | 0247565 | 6/2002 |
| WO | 02053048 A1 | 7/2002 |
| WO | 02088128 A1 | 11/2002 |
| WO | 03047446 A1 | 6/2003 |
| WO | 03090635 A1 | 11/2003 |
| WO | 03092520 A1 | 11/2003 |
| WO | 03090630 A3 | 4/2004 |
| WO | 2004028385 A1 | 4/2004 |
| WO | 2004043240 A2 | 5/2004 |
| WO | 2004047659 A2 | 6/2004 |
| WO | 2004052182 A2 | 6/2004 |
| WO | 2004073488 | 9/2004 |
| WO | 2004098385 A2 | 11/2004 |
| WO | 2004103156 | 12/2004 |
| WO | 2005046496 A1 | 5/2005 |
| WO | 2005048809 | 6/2005 |
| WO | 2005050151 | 6/2005 |
| WO | 2005060365 A2 | 7/2005 |
| WO | 2005060849 A1 | 7/2005 |
| WO | 2005115235 A1 | 12/2005 |
| WO | 2005117735 A1 | 12/2005 |
| WO | 2006050888 A1 | 5/2006 |
| WO | 2006105121 A2 | 10/2006 |
| WO | 2007055491 A1 | 5/2007 |
| WO | 2007067522 A2 | 6/2007 |
| WO | 2007076924 A2 | 7/2007 |
| WO | 2007105963 A1 | 9/2007 |
| WO | 2008002517 A1 | 1/2008 |
| WO | 2008003058 A2 | 1/2008 |
| WO | 2008011575 A1 | 1/2008 |
| WO | 2008043999 A2 | 4/2008 |
| WO | 2008044000 A1 | 4/2008 |
| WO | 2008044013 A2 | 4/2008 |
| WO | 2008053532 A1 | 5/2008 |
| WO | 2008070562 A1 | 6/2008 |
| WO | 2008071914 A2 | 6/2008 |
| WO | 2008101356 A1 | 8/2008 |
| WO | 2008110756 A2 | 9/2008 |
| WO | 2010129348 A1 | 11/2010 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944., pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence" Am. J. Mi, Jan. Mar. 1964, pp. 16-27.

Cosman et al., "Methods of Making Nervous System Lesions", in William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.

(56) References Cited

OTHER PUBLICATIONS

Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul., 1991) pp. 148-151.
Cosman et al., "Theoretical Aspects of Radiofrequency Lesions in the Dorsal Root Entry Zone", Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
U.S. Appl. No. 13/971,553 filed Aug. 20, 2013, Behnke.

\* cited by examiner

UNIVERSAL SURGICAL FOOTSWITCH TOGGLING

CROSS-REFERENCE TO RELATED APPLICATIONS

The present application claims the benefit of and priority to U.S. Provisional Patent Application No. 63/042,163 which was filed on Jun. 22, 2020. The entire contents of the foregoing applications incorporated by reference herein.

BACKGROUND

Technical Field

The present disclosure relates to systems and methods for controlling an electrosurgical generator. In particular, the present disclosure relates to controlling a plurality of electrosurgical instrument functions using a footswitch by assigning any function activatable by the instrument to the footswitch.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Conventional electrosurgical generators utilize different footswitch assemblies for each functions (e.g., one footswitch controls a corresponding electrosurgical instrument coupled to a corresponding port of an electrosurgical generator). Thus, each instrument port also has a corresponding footswitch port to accommodate an individual footswitch. Each footswitch connector port ties the footswitch assembly to the instrument connector and each footswitch can only activate a single type of surgical energy through a surgical instrument. This configuration results in excessive number of footswitches, which may be confusing to the clinician and requires a large surface area for proper setup. Thus, there is a need for a simplified footswitch control system that can control multiple electrosurgical instruments and modalities using a single footswitch.

SUMMARY

The present disclosure provides an electrosurgical system including an electrosurgical generator, a footswitch assembly, and one or more electrosurgical instruments. The footswitch includes a mode select button and one or more footswitches. When activated, the mode select button places the electrosurgical generator into a mapping state allowing for assigning an input from a button of the electrosurgical instrument or the generator to one of the footswitches. This allows for flexible use of the instruments, rather than using specific footswitches with only certain types of instruments.

According to one embodiment of the present disclosure, an electrosurgical system is disclosed. The system includes an electrosurgical generator having a radio frequency source configured to operate in a plurality of modes and a controller configured to control the radio frequency source to output a radio frequency waveform corresponding to a mode from the plurality of modes. The system also includes a footswitch assembly coupled to the electrosurgical generator. The footswitch assembly includes a footswitch in communication with the controller. The footswitch is configured to output a footswitch activation signal to activate the radio frequency source. The footswitch assembly also includes a mode select button, which upon activation, is configured to instruct the controller to enter a mapping state during which the controller assigns an activation command for one mode from the plurality of modes to the footswitch.

According to one aspect of the above embodiment, the electrosurgical system further includes an electrosurgical instrument configured to couple to the electrosurgical generator and to output the radio frequency waveform corresponding to the mode from the plurality of modes. The system may also include an ultrasonic instrument configured to couple to the electrosurgical generator and to convert the radio frequency waveform corresponding to the mode from the plurality of modes into vibrational energy. The electrosurgical instrument may further include an activation button configured to output an instrument activation signal to activate the radio frequency source, the instrument activation signal corresponding to the activation command for one mode from the plurality of modes. During the mapping state, the controller is further configured to receive the instrument activation signal to designate the activation command for assignment to the footswitch. The electrosurgical instrument may be a monopolar instrument and/or a bipolar instrument.

According to another aspect of the above embodiment, the footswitch assembly includes an indicator configured to display the mode corresponding to the activation command. The indicator may include a color-changing light and/or a display.

According to another embodiment of the present disclosure, an electrosurgical system is disclosed. The electrosurgical system includes an electrosurgical generator having a radio frequency source configured to operate in a plurality of modes; and a controller configured to control the radio frequency source to output a radio frequency waveform corresponding to a mode from the plurality of modes. The electrosurgical system also includes an electrosurgical instrument configured to couple to the electrosurgical generator and to output the radio frequency waveform corresponding to the mode from the plurality of modes. The electrosurgical instrument includes an activation button configured to output an instrument activation signal to activate the radio frequency source, the instrument activation signal corresponding to an activation command for one mode from the plurality of modes. The electrosurgical system further includes a footswitch assembly coupled to the electrosurgical generator. The footswitch assembly includes a footswitch in communication with the controller. The footswitch is configured to output a footswitch activation signal to activate the radio frequency source. The footswitch assembly further includes a mode select button, which upon activation, is configured to instruct the controller to enter a mapping state during which the controller assigns the activation command to the footswitch.

According to one aspect of the above embodiment, the electrosurgical instrument may be a monopolar instrument and/or a bipolar instrument.

According to another aspect of the above embodiment, the footswitch assembly may also include an indicator configured to display the mode corresponding to the activation command. The indicator includes a color-changing light and/or a display. The indicator may be disposed around a perimeter of the footswitch.

According to another embodiment of the present disclosure, a method for controlling an electrosurgical system is disclosed. The method includes coupling an electrosurgical instrument to an electrosurgical generator configured to operate in a plurality of modes and coupling a footswitch assembly to the electrosurgical generator. The method also includes activating a mode select button of the footswitch assembly to instruct a controller of the electrosurgical generator to enter a mapping state and activating an activation button of the electrosurgical instrument during the mapping state to output an instrument activation signal corresponding to an activation command for one mode from the plurality of modes. The method further includes assigning the activation command to a footswitch of the footswitch assembly.

According to one aspect of the above embodiment, the method includes indicating on an indicator of the footswitch assembly the mode corresponding to the activation command. Indicating may further include displaying a color indicative of the mode corresponding to the activation command. Indicating may further include displaying a name or an abbreviation of the mode corresponding to the activation command.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
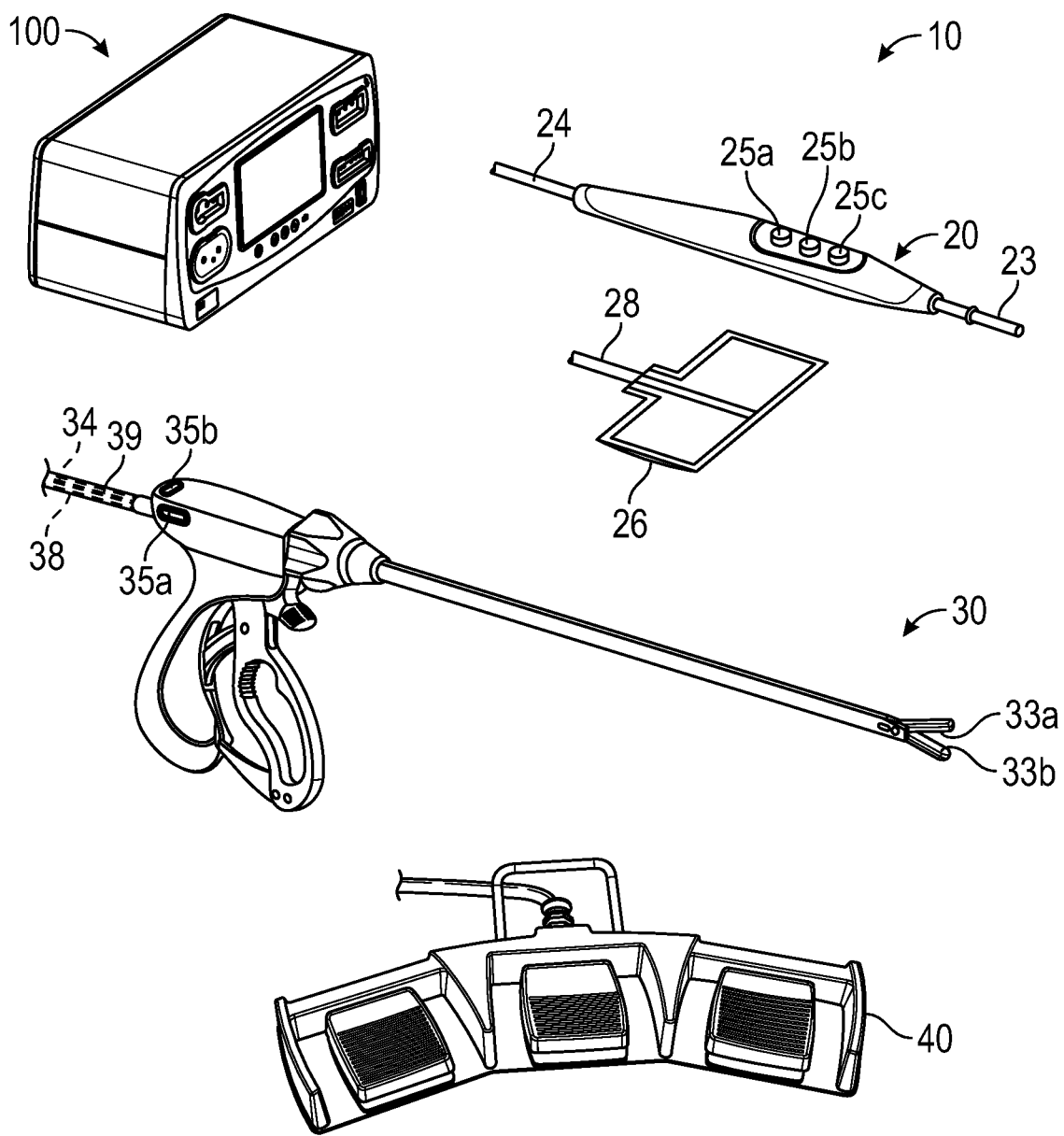
FIG. 1 is a perspective view of an electrosurgical system according to an embodiment of the present disclosure.

Embodiments of the presently disclosed electrosurgical system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, a server system, or any programmable logic device.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

Referring to FIG. 1 an electrosurgical system 10 is shown which may include a plurality of electrosurgical instruments, such as a first instrument 20 and a second instrument 30. The first instrument 20 may be a monopolar electrosurgical instrument and the second instrument 30 may be a bipolar electrosurgical instrument. The first and second instruments 20 and 30 may be ultrasonic instruments having an ultrasonic transducer configured to vibrate a waveguide/end effector. The electrosurgical system 10 also includes a footswitch assembly 40 configured to control operation of either the first instrument 20 or the second instrument 30. In embodiments, the electrosurgical system 10 may operate with hybrid monopolar/bipolar electrosurgical instruments.

First instrument 20 include one or more active electrodes 23 (e.g., electrosurgical cutting probe, ablation electrode(s), etc.) for treating tissue of a patient. The system 10 may include a plurality of return electrode pads 26 that, in use, are disposed on a patient to minimize the chances of tissue damage by maximizing the overall contact area with the patient. Electrosurgical alternating RF current is supplied to the first instrument 20 by a generator 100 via supply line 24. The alternating RF current is returned to the generator 100 through the return electrode pad 26 via a return line 28. In addition, the generator 100 and the return electrode pads 26 may be configured for monitoring tissue-to-patient contact to ensure that sufficient contact exists therebetween. The first instrument 20 includes a plurality of activation buttons 25a, 25b, 25c, each of which is configured to activate the electrosurgical generator 100 to operate in a corresponding mode and output an electrosurgical waveform for treating tissue.

Second instrument 30 is shown as forceps. In embodiments, the second instrument 30 may be tweezers. The second instrument 30 includes a pair of electrodes 33a and 33b for treating tissue of a patient, which are connected to the electrosurgical generator 100 through a cable 39 that includes the supply and return lines 34, 38. The second instrument 30 is coupled to the electrosurgical generator 100 at a port having connections to the active and return terminals (e.g., pins) via a plug (not shown) disposed at the end of the cable 39, wherein the plug includes contacts from the supply and return lines 34, 38 as described in more detail below. The second instrument 30 includes a plurality of activation buttons 35a and 35b each of which is configured to activate the electrosurgical generator 100 to operate in a corresponding mode and output an electrosurgical waveform for treating tissue.

Figure 2:
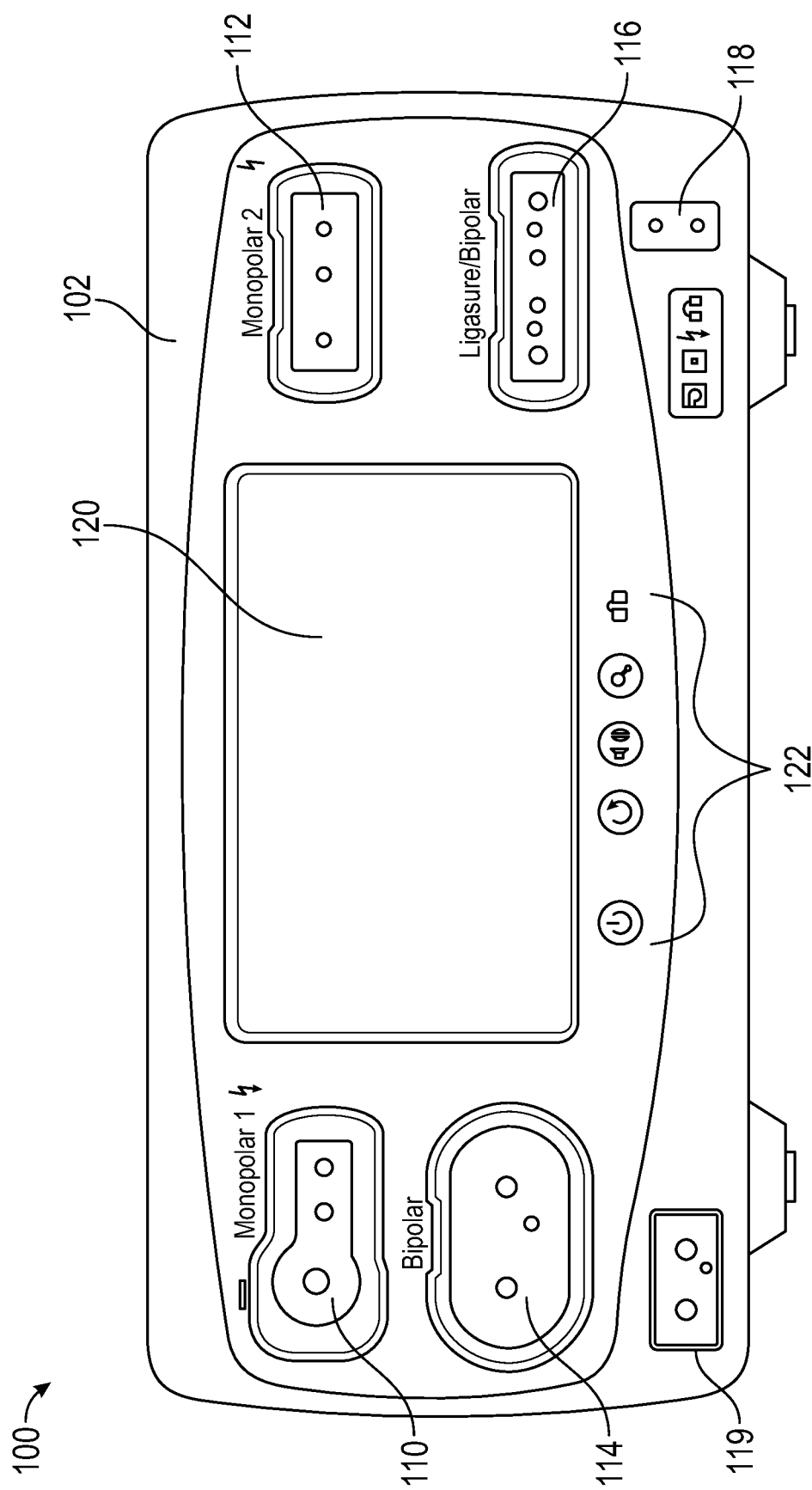
FIG. 2 is a front view of a dual RF source electrosurgical generator of FIG. 1 according to an embodiment of the present disclosure.

With reference to FIG. 2, a front face 102 of the generator 100 is shown. The generator 100 may include a plurality of ports 110, 112, 114, 116 to accommodate various types of electrosurgical instruments and a port 118 for coupling to the return electrode pad 26 and a port 119 configured to couple to the footswitch assembly 40. The ports 110 and 112 are configured to couple to the first instrument 20. The ports 114 and 116 are configured to couple to the bipolar electrosurgical instruments 30. The generator 100 includes a display 120 for providing the user with variety of output information (e.g., intensity settings, treatment complete indicators, etc.). The display 120 is a touchscreen configured to display a menu corresponding to each of the ports 110, 112, 114, 116 and the instrument coupled. The user also adjusts inputs by touching corresponding menu options. The generator 100 also includes suitable input controls 122 (e.g., buttons, activators, switches, touch screen, etc.) for controlling the generator 100.

The generator 100 is configured to operate in a variety of modes and is configured to output monopolar and/or bipolar waveforms corresponding to the selected mode. Each of the modes may be activated by the buttons 25a, 25b, 25c of the first instrument 20 and the buttons 35a and 35b of the second instrument 30 and/or the footswitch assembly 40. Each of the modes operates based on a preprogrammed power curve that limits how much power is output by the generator 100 at varying impedance ranges of the load (e.g., tissue). Each of the power curves includes power, voltage and current control ranges that are defined by the user-selected intensity setting and the measured minimum impedance of the load.

The generator 100 may operate in the following monopolar modes, which include, but are not limited to, cut, blend, division with hemostasis, fulgurate and spray. The generator 100 may operate in the following bipolar modes, including bipolar cutting, bipolar coagulation, automatic bipolar which operates in response to sensing tissue contact, and various algorithm-controlled vessel sealing modes.

Each of the RF waveforms may be either monopolar or bipolar RF waveforms, each of which may be continuous or discontinuous and may have a carrier frequency from about 200 kHz to about 500 kHz. As used herein, continuous waveforms are waveforms that have a 100% duty cycle. In embodiments, continuous waveforms are used to impart a cutting effect on tissue. Conversely, discontinuous waveforms are waveforms that have a non-continuous duty cycle, e.g., below 100%. In embodiments, discontinuous waveforms are used to provide coagulation effects to tissue.

Figure 3:
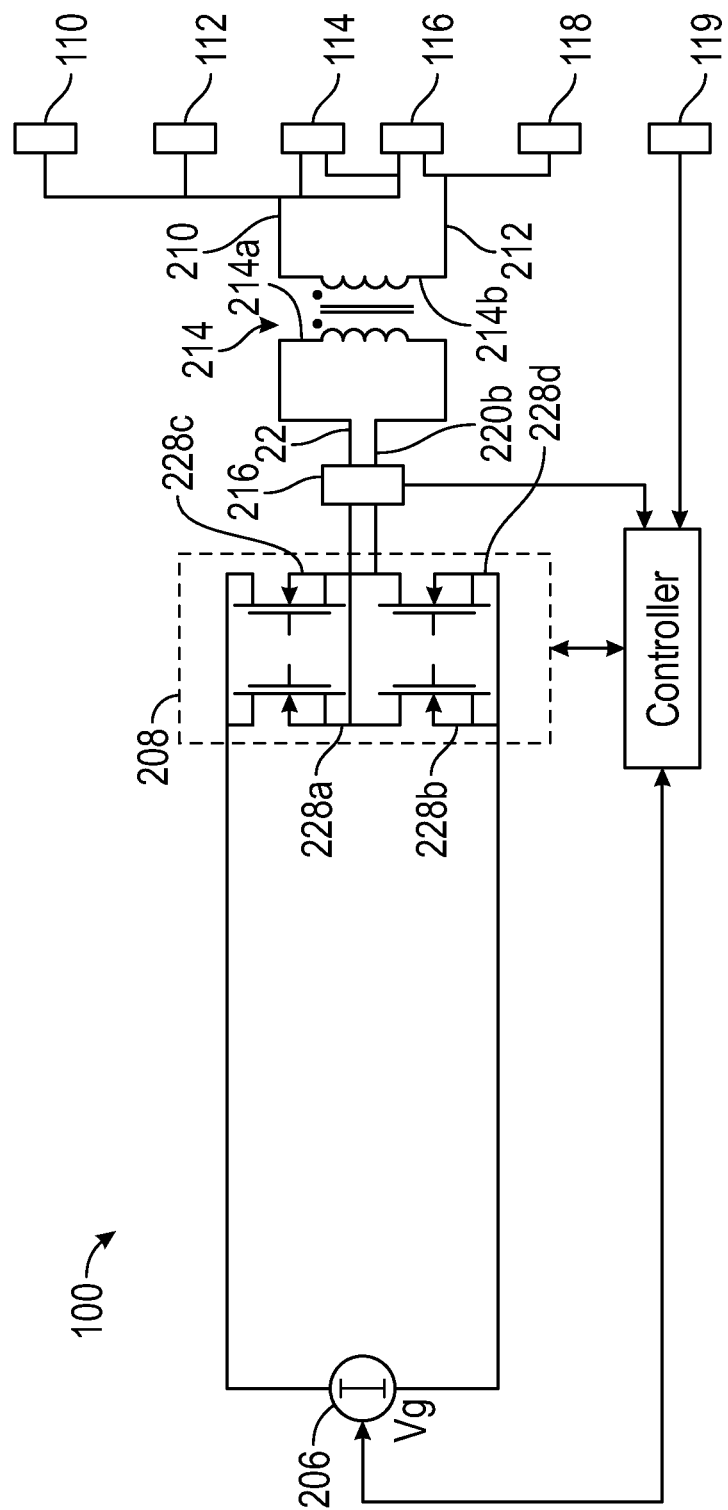
FIG. 3 is a schematic diagram of the electrosurgical generator of FIG. 1 according to an embodiment of the present disclosure.

With reference to FIG. 3, the generator 100 includes a controller 204, a power supply 206, and a RF inverter 208. The power supply 206 may be high voltage, DC power supplies connected to a common AC source (e.g., line voltage) and provide high voltage, DC power to their respective RF inverter 208, which then convert DC power into a RF waveform through active terminal 210 and return terminal 212 corresponding to the selected mode.

The active terminal 210 and the return terminal 212 are coupled to the RF inverter 208 through an isolation transformer 214. The isolation transformer 214 includes a primary winding 214a coupled to the RF inverter 208 and a secondary winding 214b coupled to the active and return terminals 210 and 212.

Electrosurgical energy for energizing the first instrument 20 is delivered through the ports 110 and 112, each of which is coupled to the active terminal 210. RF energy is returned through the return electrode pad 26 coupled to the port 118, which in turn, is coupled to the return terminal 212. The secondary winding 214b of the isolation transformer 214 is coupled to the active and return terminals 210 and 212. RF energy for energizing the second instrument 30' is delivered through the ports 114 and 116, each of which is coupled to the active terminal 210 and the return terminal 212. The generator 100 may include a plurality of steering relays or other switching devices configured to couple the active terminal 210 and the return terminals 212 to various ports 110, 112, 114, 116, 118 based on the combination of the monopolar and bipolar electrosurgical instruments 20 and 30 being used.

The RF inverter 208 is configured to operate in a plurality of modes, during which the generator 100 outputs corresponding waveforms having specific duty cycles, peak voltages, crest factors, etc. It is envisioned that in other embodiments, the generator 100 may be based on other types of suitable power supply topologies. RF inverter 208 may be a resonant RF amplifier or non-resonant RF amplifier, as shown. A non-resonant RF amplifier, as used herein, denotes an amplifier lacking any tuning components, i.e., conductors, capacitors, etc., disposed between the RF inverter and the load, e.g., tissue.

The controller 204 may include a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 204 is operably connected to the power supply 206 and/or RF inverter 208 allowing the processor to control the output of the RF source 202 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to the controller 204. The controller 204 then controls the power supply 206 and/or RF inverter 208, which adjust the DC and/or RF waveform, respectively.

The generator 100 according to the present disclosure may also include a plurality of sensors 216, each of which monitors output of the RF source 202 of the generator 100. The sensor 216 may be any suitable voltage, current, power, and impedance sensors. The sensors 216 are coupled to leads 220a and 220b of the RF inverter 208. The leads 220a and 220b couple the RF inverter 208 to the primary winding 214a of the transformer 214. Thus, the sensors 216 are configured to sense voltage, current, and other electrical properties of energy supplied to the active terminal 210 and the return terminal 212.

In further embodiments, the sensor 216 may be coupled to the power supply 206 and may be configured to sense properties of DC current supplied to the RF inverter 208. The controller 204 also receives input (e.g., activation) signals from the display 120, the input controls 122 of the generator 100 and/or the instruments 20 and 30 (e.g., buttons 25a, 25b, 25c, 35a, 35b), and the footswitch assembly 40. The controller 204 adjust power outputted by the generator 100 and/or perform other control functions thereon in response to the input signals.

The RF inverter 208 includes a plurality of switching elements 228a-228d, which are arranged in an H-bridge topology. In embodiments, RF inverter 208 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicon carbide, or any other suitable wide bandgap materials.

The controller 204 is in communication with the RF inverters 208, and in particular, with the switching elements 228a-228d. Controller 204 is configured to output control signals, which may be pulse-width modulated ("PWM") signals, to switching elements 228a-228d. In particular, controller 204 is configured to modulate a control signal supplied to switching elements 228a-228d of the RF inverter 208. The control signal provides PWM signals that operate the RF inverter 208 at a selected carrier frequency. Additionally, controller 204 are configured to calculate power characteristics of output of the RF source 202 of the generator 100, and control the output of the generator 100 based at least in part on the measured power characteristics including, but not limited to, voltage, current, and power at the output of RF inverters 208.

Figure 4:
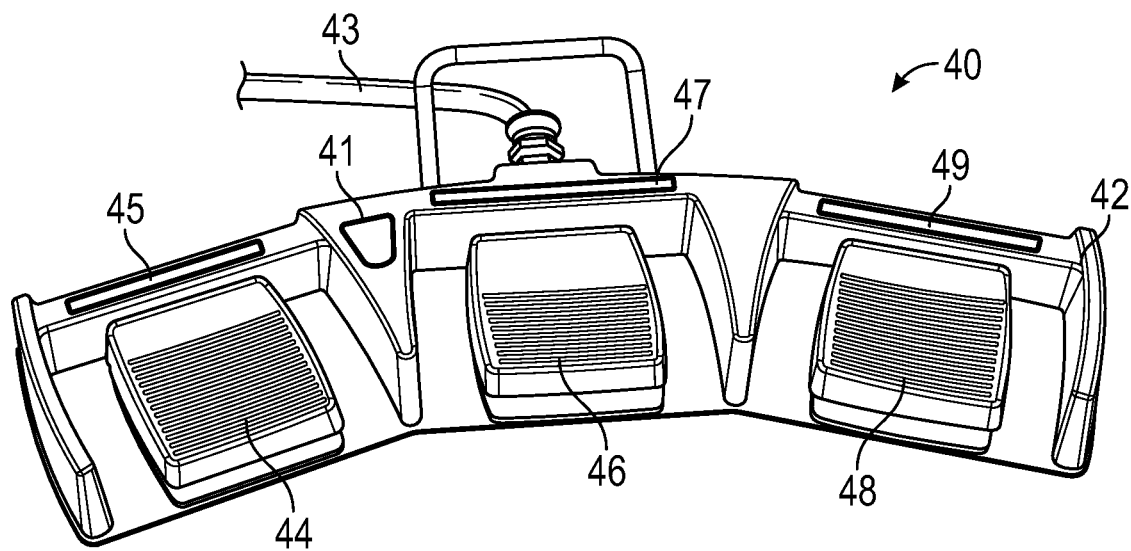
FIG. 4 is a perspective view of a footswitch according to one embodiment of the present disclosure.

With reference to FIG. 4, the footswitch assembly 40 includes a base housing 42 accommodating a plurality of footswitches 44, 46, 48, which are shown as pedal switches. The footswitches 44, 46, 48 may be any mechanically actuated electrical switch such as a toggle switch, a push-button switch, which requires continuous engagement, and combinations thereof (e.g., a pushbutton latching switch or a pushbutton continuous switch). The footswitches 44, 46, 48 may be on-off switches, latching switches, continuous switches, and the like. As used herein a latching switch maintains the state in which the switch was placed following last engagement. When activated, the footswitches 44, 46, 48 output activation signals to the controller 204, which then activates a selected mode and output an electrosurgical waveform.

The footswitch assembly 40 is coupled to the port 119 of the generator via a cable 43 and is coupled to the controller 204. This allows the footswitch assembly 40 to transmit activation signals to the controller 204 and for the controller 204 to reconfigure operation of the footswitch assembly 40. The footswitch assembly 40 is configured to control any of the instruments coupled to any of the ports 110, 112, 114, 116 of the generator 100. This is accomplished by configuring operation of the footswitch assembly 40. Configuration of the footswitch assembly 40 may be done at any point during use of the generator 100. The footswitch assembly 40 includes a mode select button 41, which allows for assigning any one of the footswitches 44, 46, 48 to a particular button function of the instrument 20 or 30. In embodiments, the footswitches 44, 46, 48 may be mapped to any one of the functions or modes that are activated by the buttons 25a, 25b, 25c of the monopolar instrument 20 or the buttons 35a and 35b of the bipolar instrument 30. Thus, the footswitches 44 and 46 may be mapped to the buttons 25a and 25b while the footswitch 48 may be mapped to the button 35a. In further embodiments, the footswitches 44, 46, 48 may be mapped to any of the modes or functions that are activated using the interface of the generator 100, namely, through the display 120 and the input controls 122.

Mapping of the modes may be accomplished by initially pressing the mode select button 41. This instructs the controller 204 to enter a mapping state during which the controller 204 is configured to receive an activation signal from the instrument 20, 30, or the generator 100 and maps an activation command corresponding to the activation signal to one of the footswitches 44, 46, 48. Thus, the controller 204 waits for engagement of one of the buttons 25a, 25b, 25c of the monopolar instrument 20, the buttons 35a and 35b of the bipolar instrument 30, or on the display 120 and the input controls 122 of the generator 100. After the mode is selected, the user then engages one of the footswitches 44, 46, 48 and the mode activation command is mapped to the engaged footswitch 44, 46, 48. In embodiments, the mode select button 41 may be pressed continuously while the mapping process is performed, this indicates to the controller 204 to disengage any RF power application and to map the selected function to the footswitch assembly 40.

During mapping of functions to the footswitch assembly 40, the generator 100 may display the order of steps to map the functions on the display 120, such that the user is guided through the process and to further indicate that the function has been successfully mapped. In embodiments, the order of selecting the function to be mapped and selecting which of the footswitches 44, 46, 48 is being mapped may be reversed, such that the user initially selects the footswitch 44, 46, 48 followed by selection of the function. Once the function is mapped to one of the footswitches 44, 46, 48 the user may then continue to activate that function by pressing the footswitch 44, 46, 48. The assigned function of the footswitch 44, 46, 48 may be overwritten at any time by pressing the mode select button 41 and repeating the assignment process.

The footswitch assembly 40 also includes indicators 45, 47, 49 corresponding to each of the footswitches 44, 46, 48, respectively. Each of the indicators 45, 47, 49 is configured to indicate to the user the currently assigned function. The indicators 45, 47, 49 may be displays configured to display the currently assigned function or instrument using text (e.g., name, abbreviation and/or numbers). The displayed information may also be color-coded. In further embodiments, the indicators 45, 47, 49 may be color-changing lights (e.g., full-spectrum LEDs) configured to change color to a predefined color associated with the function or port 110, 112, 114, 116 of the generator 100. The assigned color of each of the ports 110, 112, 114, 116 may be shown on the display 120 such that the assigned color corresponds to the color on the graphical user interface of the display 120. The indicators 45, 47, 49 may be of any suitable shape or size that is visible by the user.

Figure 5:
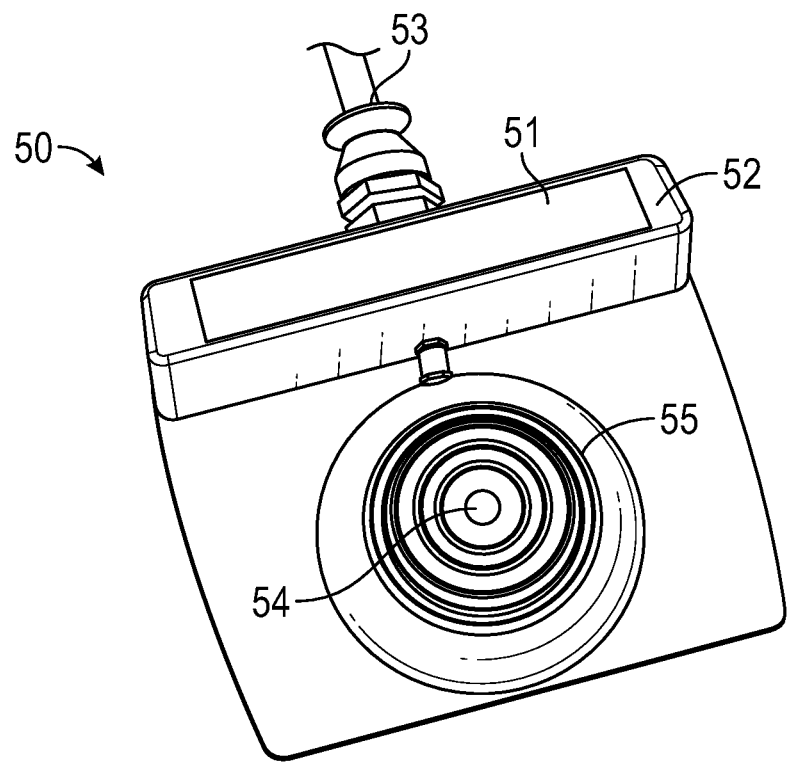
FIG. 5 is a perspective view of a footswitch according to another embodiment of the present disclosure.

Another embodiment of the footswitch assembly 50 is shown in FIG. 5. The footswitch assembly 50 has the same components and performs the same function as the footswitch assembly 40, in which like reference numerals designate identical or corresponding elements, however, the differences are described below. The footswitch assembly 50 includes a base housing 52 having a single footswitch 54, a cable 53 coupling the footswitch assembly 50 to the generator 100, a mode select button 51, and an indicator 55. The footswitch assembly 50 is substantially similar to the footswitch assembly 40 except that the footswitch assembly 50 includes only one footswitch 54, which is shown as a pushbutton switch. In addition, the indicator 55 is shown as a lighted outline (e.g., a light ring) disposed around the footswitch 54 and is configured to change color based on the selected function, which is accomplished in the manner described above with respect to the footswitch assembly 40. In embodiments, the indicator 55 may have any suitable shape conforming to the outline of the footswitch 54, e.g., a rectangular footswitch 54 may have a rectangular outline along the perimeter of the footswitch 54. In further embodiments, the indicator 55 may be a display that is also shaped to conform to the shape of the footswitch 54. The generator 100 may include a plurality of ports 119 such that any number of footswitch assemblies 40 or 50 may be used. In further embodiments, footswitch assemblies may include any number of footswitches.

Figure 6:
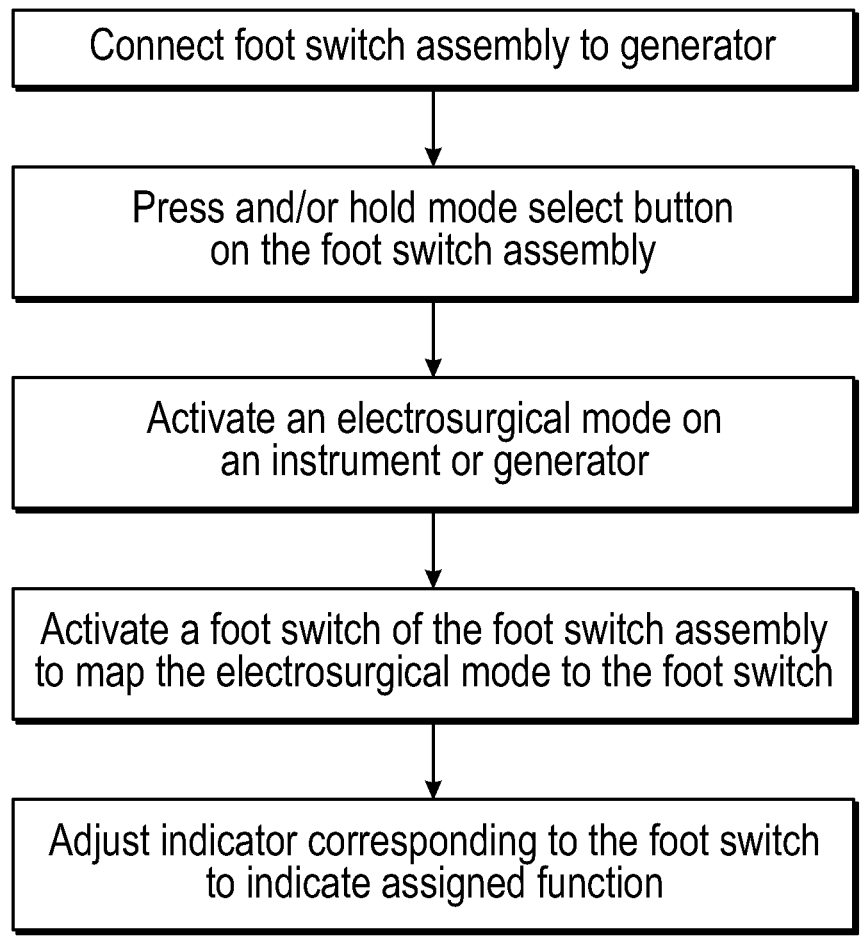
FIG. 6 is a flow chart of a method for operating the electrosurgical generator of FIG. 1 according to an embodiment of the present disclosure.

With reference to FIG. 6, a method of configuring and using the footswitch assembly 40 is described. The footswitch assembly 50 may be used the same method. Initially, the footswitch assembly 40 is connected to the port 119 of the generator 100. The controller 204 may be configured to detect that the footswitch assembly 40 is properly connected to the port 119 and/or the footswitch assembly 40 is an approved accessory. In addition, one or more of the first instrument 20 and/or the second instrument 30 are also coupled to the generator 100 through one of the ports 110, 112, 114, 116. The user may also configure the generator 100 to operate in a corresponding electrosurgical mode by modifying settings (e.g., intensity).

Thereafter, the user engages the mode select button 41 of the footswitch assembly 40 to commence function assignment to one of the footswitches 44, 46, 48. The mode select button 41 may be pressed and/or held during assignment. Thereafter, the user activates the electrosurgical mode by engaging of one of the buttons 25a, 25b, 25c of the monopolar instrument 20 or the buttons 35a and 35b of the bipolar instrument 30 or on the display 120 and the input controls 122 of the generator 100.

After the mode is selected, the user then engages one of the footswitches 44, 46, 48 to select to which of the footswitches 44, 46, 48 the mode activation command is mapped. In embodiments, the mode select button 41 may be pressed continuously while the mapping process is performed, this indicates to the controller 204 to disengage any RF power application and to map the selected function to the footswitch assembly 40.

In embodiments, the order of selecting the function to be mapped and selecting which of the footswitches 44, 46, 48 the function is mapped to may be reversed, such that the user initially selects the footswitch 44, 46, 48 followed by selection of the function. The controller 204 maps the function to the selected footswitch 44, 46, 48 and also adjusts the corresponding indicator 45, 47, 49 to display the assigned function. Thereafter, the user may activate the assigned function by engaging one of the footswitches 44, 46, 48.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical system comprising:
   an electrosurgical generator including:
      a radio frequency source configured to operate in a plurality of modes;
      a controller configured to control the radio frequency source to output a radio frequency waveform corresponding to a mode from the plurality of modes; and
      input controls configured to receive a user input selecting one mode from the plurality of modes; and
   a footswitch assembly coupled to the electrosurgical generator, the footswitch assembly including:
      a footswitch in communication with the controller, the footswitch configured to output a footswitch activation signal to activate the radio frequency source; and
      a mode select button, which upon activation, is configured to instruct the controller to enter a mapping state during which the controller assigns an activation command for the selected mode from the input controls to the footswitch.

2. The electrosurgical system according to claim 1, further comprising:
   an electrosurgical instrument configured to couple to the electrosurgical generator and to output the radio frequency waveform corresponding to the mode from the plurality of modes.

3. The electrosurgical system according to claim 2, wherein the electrosurgical instrument further includes an activation button configured to output an instrument activation signal to activate the radio frequency source, the instrument activation signal corresponding to the activation command for the selected mode from the plurality of modes.

4. The electrosurgical system according to claim 3, wherein during the mapping state the controller is further configured to receive the instrument activation signal to designate the activation command for assignment to the footswitch.

5. The electrosurgical system according to claim 2, wherein the electrosurgical instrument is a monopolar instrument.

6. The electrosurgical system according to claim 2, wherein the electrosurgical instrument is a bipolar instrument.

7. The electrosurgical system according to claim 1, wherein the footswitch assembly includes an indicator configured to display the mode corresponding to the activation command.

8. The electrosurgical system according to claim 7, wherein the indicator includes a color-changing light.

9. The electrosurgical system according to claim 7, wherein the indicator includes a display.

10. The electrosurgical system according to claim 1, further comprising:
    an ultrasonic instrument configured to couple to the electrosurgical generator and to convert the radio frequency waveform corresponding to the mode from the plurality of modes into vibrational energy.

11. An electrosurgical system comprising:
    an electrosurgical generator including:
       a radio frequency source configured to operate in a plurality of modes; and a controller configured to control the radio frequency source to output a radio frequency waveform corresponding to a mode from the plurality of modes; and
input controls configured to receive a user input selecting one mode from the plurality of modes; and
an electrosurgical instrument configured to couple to the electrosurgical generator and to output the radio frequency waveform corresponding to the selected mode from the plurality of modes, the electrosurgical instrument including an activation button configured to output an instrument activation signal to activate the radio frequency source, the instrument activation signal corresponding to an activation command for the selected mode from the input controls; and
a footswitch assembly coupled to the electrosurgical generator, the footswitch assembly including:
a footswitch in communication with the controller, the footswitch configured to output a footswitch activation signal to activate the radio frequency source; and
a mode select button, which upon activation, is configured to instruct the controller to enter a mapping state during which the controller assigns the activation command for the selected mode from the input controls to the footswitch.

12. The electrosurgical system according to claim 11, wherein the electrosurgical instrument is a monopolar instrument.

13. The electrosurgical system according to claim 11, wherein the electrosurgical instrument is a bipolar instrument.

14. The electrosurgical system according to claim 11, wherein the footswitch assembly includes an indicator configured to display the mode corresponding to the activation command.

15. The electrosurgical system according to claim 14, wherein the indicator includes a color-changing light.

16. The electrosurgical system according to claim 14, wherein the indicator includes a display.

17. The electrosurgical system according to claim 14, wherein the indicator is disposed around a perimeter of the footswitch.

18. A method for controlling an electrosurgical system, the method comprising:
coupling an electrosurgical instrument to an electrosurgical generator configured to operate in a plurality of modes;
receiving a user input selecting one mode from the plurality of modes at input controls of the electrosurgical generator;
coupling a footswitch assembly to the electrosurgical generator;
activating a mode select button of the footswitch assembly to instruct a controller of the electrosurgical generator to enter a mapping state;
activating an activation button of the electrosurgical instrument during the mapping state to output an instrument activation signal corresponding to an activation command for the selected mode from the input controls; and
assigning the activation command to a footswitch of the footswitch assembly.

19. The method according to claim 18, further comprising:
indicating on an indicator of the footswitch assembly the mode corresponding to the activation command.

20. The method according to claim 19, wherein indicating further includes displaying at least one of a color, a name, or an abbreviation indicative of the mode corresponding to the activation command.

* * * * *